United States Patent [19]
Coates

[11] Patent Number: 5,409,476
[45] Date of Patent: Apr. 25, 1995

[54] REUSABLE DIAPER HAVING GUSSETED PAD INSERT

[76] Inventor: Fredrica Coates, 960 Madison Dr., Earlysville, Va. 22936

[21] Appl. No.: 104,700

[22] Filed: Aug. 11, 1993

[51] Int. Cl.⁶ ............................................. A61F 13/15
[52] U.S. Cl. ................................ 604/391; 604/385.1; 604/385.2
[58] Field of Search .................. 604/385.1, 385.2, 386, 604/387, 391, 392, 397, 398

[56] References Cited

U.S. PATENT DOCUMENTS

| | | | |
|---|---|---|---|
| Re. 28,483 | 7/1975 | Ralph | 604/397 |
| 1,989,283 | 1/1935 | Limacher . | |
| 2,545,761 | 3/1951 | Brinks | 604/397 |
| 2,558,215 | 6/1951 | Habig et al. . | |
| 2,571,577 | 10/1951 | Howard . | |
| 2,684,677 | 7/1954 | Pinney . | |
| 2,743,725 | 5/1956 | Matthews . | |
| 3,349,769 | 10/1967 | Piekarski . | |
| 3,386,443 | 6/1968 | Goldstein . | |
| 3,563,242 | 2/1971 | Hedstrom | 604/392 |
| 3,568,676 | 3/1971 | Del Guercio . | |
| 3,653,381 | 4/1972 | Warnken . | |
| 3,838,693 | 10/1974 | Sherman . | |
| 3,955,575 | 5/1976 | Okuda . | |
| 4,475,912 | 10/1984 | Coates . | |
| 4,537,591 | 3/1985 | Coates . | |
| 4,578,073 | 3/1986 | Dysart et al. | 604/397 |
| 4,680,030 | 7/1987 | Coates et al. . | |
| 4,681,581 | 7/1987 | Coates . | |
| 4,695,278 | 9/1987 | Lawson | 604/385.2 |
| 4,704,117 | 11/1987 | Mitchell . | |
| 4,728,326 | 3/1988 | Gilles . | |
| 4,773,906 | 9/1988 | Krushel . | |
| 4,801,298 | 1/1989 | Sorenson et al. . | |
| 4,808,177 | 2/1989 | DesMarais et al. | 604/385.1 |
| 4,850,987 | 7/1989 | Gilomen . | |
| 4,961,736 | 10/1990 | McCloud . | |
| 5,069,672 | 12/1991 | Wippler et al. | 604/395 |
| 5,137,526 | 8/1992 | Coates . | |
| 5,209,743 | 5/1993 | Hardison | 604/391 |
| 5,217,447 | 6/1993 | Gagnon | 604/391 |

FOREIGN PATENT DOCUMENTS

0475702  3/1992  European Pat. Off. ............ 604/391

*Primary Examiner*—Randall L. Green
*Assistant Examiner*—Rob Clarke
*Attorney, Agent, or Firm*—Lowe, Price, LeBlanc & Becker

[57] ABSTRACT

A reusable infant or adult diaper comprises a fluid absorbent pad on the inner surface of a waterproof, hourglass-shaped, diaper shell. Extending from the rear corners of the diaper shell is a pair of fastener tabs carrying filamentary hook fastener material. Slightly larger strips of filamentary loop material on the inner surface of the diaper shell cover the fastener tabs during washing to protect the filamentary hook material from buildup of lint. Each fastener tab and its cover, assembled to the diaper shell by a single continuous line of stitching and turned to the inside of the diaper, presents a finished edge at a corner of the diaper shell. The diaper is fitted to the infant or adult by wrapping the shell around the pelvic region and coupling the fastener tabs to a pair of strips carrying filamentary loop material and arranged in a V-pattern on the front of the diaper. Several embodiments of the diaper are disclosed, including different mechanisms to fasten the shell and absorbent material to the body of the wearer. Fasteners attached to the diaper may be detachable therefrom. Absorbent material may be sewn into the shell or be floating in the shell between the leg holes of the diaper.

9 Claims, 10 Drawing Sheets

REUSABLE DIAPER HAVING GUSSETED PAD INSERT

TECHNICAL FIELD

This invention relates generally to reusable diapers, and more particularly to a reusable diaper of a type using filamentary fasteners, rather than pins or clips, to retain the diaper to an infant or adult. The invention relates further to an improved method of attaching filamentary fasteners to the diaper during manufacture.

BACKGROUND ART

To enhance safety for infants and adult home health care patients as well as promote preservation of the ecology, there is a trend by consumers to return to use of reusable, rather than disposable, infant and adult diapers. A recent improvement to reusable diapers is in the replacement of pin fasteners by fasteners of filamentary material, such as hook and loop filamentary material manufactured by Velcro Corporation and Aplix Corporation. In this regard, reference is made to my previous U.S. Pat. No. 4,537,591 which discloses a cloth diaper having filamentary fasteners together with a self-closing tab cover that protects the fasteners from buildup of lint during washing.

Consumers of cloth diapers, particularly of fitted diapers, are very sensitive to cost as well as to convenience of use of the product. As the cost of materials forming the cloth diaper is relatively fixed, differences in price among similar reusable diapers depend significantly on cost of manufacturing.

In addition to cost and convenience, marketability of such diapers depends on the tailoring of the product, that is, not only on whether the diaper functions adequately in the manner intended but also on whether the diaper has a good finished appearance. The diaper should have no rough or raw edges visible and no other evidence of apparent poor workmanship. The diaper furthermore must adequately absorb and direct fluid away from clothing and from surrounding bedding, even when worn by an infant or adult in the prone position, and must be capable of drying quickly. To prevent leakage of fluid, any piercing of waterproof material by stretching should be avoided. The diaper should be configured to cup the groin of the wearer so as to encase fluid.

In addition to all these requirements, safety of any diaper to an infant or adult wearing it is paramount to any design. The infant or adult must be incapable of removing the diaper himself and lifting it to the region of his head.

DISCLOSURE OF THE INVENTION

Accordingly, one object of the invention is to improve construction of a reusable diaper.

Another object of the invention is to minimize the cost of producing a reusable diaper having filamentary fasteners for retaining the diaper to a wearer.

A further object is to produce an improved reusable diaper that is effective to absorb and direct fluid away from clothing worn by a wearer and from surrounding bedding.

A still further object is to produce an improved diaper of a type having filamentary fasteners that do not accumulate lint during washing.

Another object of the invention is to entrap fluid in an infant or adult diaper even while the infant or adult is in the prone position.

Another object is to provide a diaper that is adjustable in size, and at any size is effective to entrap fluid.

A further object of the invention is to enhance safety of reusable diapers to infants or adults wearing them.

A more specific object is to enhance safety of reusable diapers to infants or adults by inhibiting the infant or adult from removing the diaper through manual manipulation of diaper fasteners.

Another object is to reduce the amount of time required to dry a moisture-laden diaper following washing.

A further object is to mount a fluid absorbent pad to a diaper shell in such a manner as not to pierce the surface of the shell by any stitching.

Still another object of the invention is to provide a reusable diaper that cups the groin of a wearer to encase fluid.

The above and other objects of the invention are satisfied by a reusable diaper comprising a waterproof diaper shell, a fluid absorbent pad retained on an inner surface of the diaper shell and a pair of fastener tabs carrying one type of filamentary fastener material (e.g., hook) and extending from rear corners of the shell. Cover strips of filamentary fastener material of the opposite type (loop) on the inner surface of the diaper shell are positioned to couple to the fastener tabs during washing so as to protect the filamentary material on the tabs from buildup of lint. The base of each fastener tab and the periphery of a corresponding tab cover strip are attached to the diaper shell by a continuous line of stitching. A region of fastener material of the opposite type is positioned on the outside of the diaper shell to couple to the fastener tabs when the diaper is worn. A single line of continuous stitching, attaching both the fastener tab and cover strip to the exterior surface of the diaper shell, presents a sealed edge having a finished appearance at each corner of the diaper and minimizes its cost of manufacture. The raw edge of the diaper at each tab and strip is sealed by material turned to the inside of the shell during formation of the continuous stitching.

In one embodiment, the fastener material on the exterior surface of the frontal portion of the diaper comprises a pair of strips arranged in a V-pattern. Only upper and lower ends of the fluid absorbent pad are retained to the interior surface of the diaper shell, and the end of the shell at the interior frontal portion of the diaper is folded to form a pocket to retain the pad by a V-shaped run of stitching. The opposite end of the pad is retained to the shell by encasement by a strip of fabric forming a folded trim.

As a further feature of the preferred embodiment, the diaper shell has an hourglass shape to fit the form of the infant or adult. The edge of the shell is finished by a folded trim.

In accordance with another aspect of the invention, the diaper comprises a waterproof diaper shell and a pair of fastener tabs carrying one type of filamentary fastener material and extending from corners of the diaper shell. Cover strips of opposite type filamentary fastener material positioned on the interior surface of the diaper shell couple to the fastener tabs during washing so as to protect hook-type filamentary material on the tabs from buildup of lint. A region of opposite type filamentary fastener material is positioned on the exterior surface of the diaper shell to couple to the fastener tabs when the diaper is worn. A fluid absorbent pad is retained only by its upper and lower ends on the inner surface of the diaper shell; the remainder of the pad "floats" on the shell. This structure retains the pad within the shell while preventing the fluid-exposed portions of the shell from being penetrated by any additional stitching. The floating pad also dries quickly following washing since both its outer surfaces are exposed to air.

The fastener tabs and covers are attached to the diaper by coupling each fastener tab and cover strip together and positioning them at a corner on the outer surface of the shell. In this position, the raw edges of the diaper shell, tab and cover are in juxtaposition and the cover is on top of the tab. Stitching is formed along the inner edge of fastener tab and tab cover. Next, the tab and cover, together with a portion of the diaper shell having the stitching are turned to the inner surface of the diaper shell and the stitching is continued along the periphery of the cover for attachment to the shell.

Other features of the invention include:
- a fluid isolation "bumper" between one end of the fluid absorbent pad and the diaper shell, to restrict fluid flow from the pad to the wearer;
- the pad mounted to the shell on a waterproof "sling", and one end of the sling extending beyond the pad to form the bumper;
- a central portion of the fluid absorbent pad formed with a "tuck" for improved absorbency;
- the sides of the pad encased by a folded trim that may be formed of an elastic material, to cup the groin and enhance fluid encasement;
- fluid isolation "gussets" of waterproof material at opposite sides of the diaper shell, cupping the groin near the thighs of the wearer;
- triangular filamentary fastener region on the exterior surface of the diaper shell;
- a belt and fastener assembly, supplementing the filamentary fastener tabs, to retain the diaper to the wearer; and
- a belt carrying the filamentary fastener tabs for retaining the diaper to the wearer, wherein the belt may be adjustable in length.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF THE DRAWINGS

FIG. 4A is a second view of a sixth embodiment of the invention including an additional belt and fastener assembly as a safety feature to retain the diaper to an infant or adult.

FIG. 4B is a third view of a sixth embodiment of the invention including an additional belt and fastener assembly as a safety feature to retain the diaper to an infant or adult.

BEST MODE FOR CARRYING OUT THE INVENTION

Figure 5:
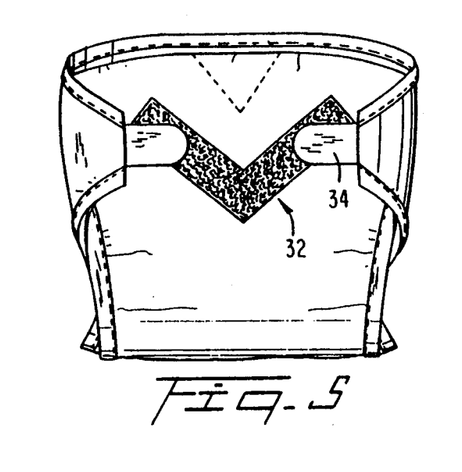
FIG. 5 shows the fastener tabs coupled to the V-shaped fastener region.
Figure 6:
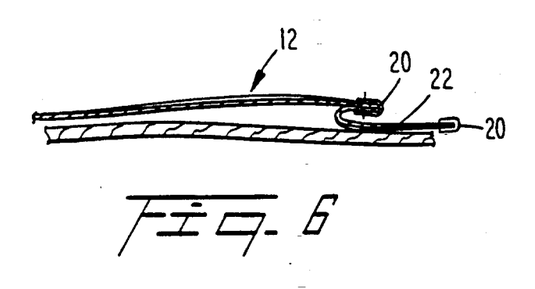
FIG. 6 is a cross-sectional view of the diaper taken along the line 6—6 in FIG. 2.
Figure 7:
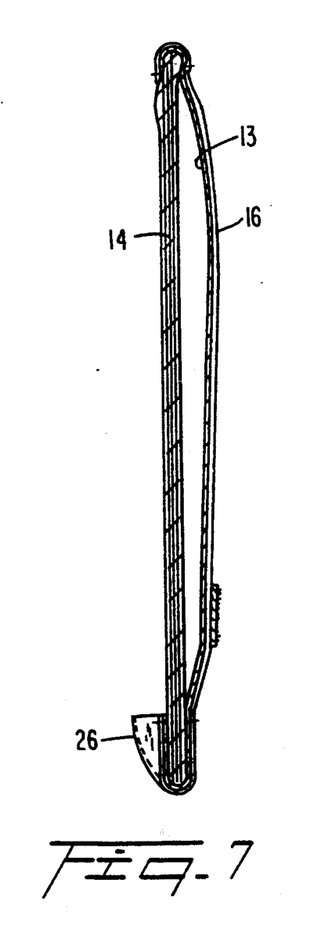
FIG. 7 is a cross-sectional view of the diaper taken along the line 7—7 in FIG. 3.
Figure 8:
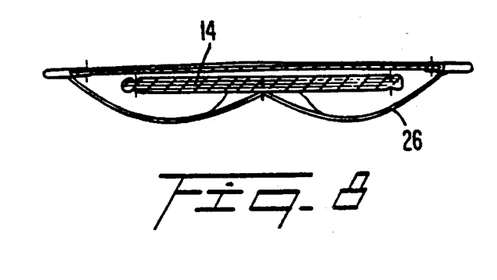
FIG. 8 is a cross-sectional view of the diaper taken along the line 8—8 in FIG. 2.

Referring to FIGS. 1-8, a reusable diaper in accordance with one embodiment of the invention, designated generally as 10, comprises a waterproof diaper shell 12 within which is retained a fluid absorbent pad 14 positioned to be located about the groin when worn by an infant or adult. The shell 12 is formed of two layers; a waterproof layer 16 (e.g., nylon) is on the outside of an inner cloth layer 18 as shown in FIG. 7. The two layers 16 and 18 are retained together by a folded trim 20 formed of Lycra® or similar material, stitched to the edges of the layers. The inner layer 18 presents a comfortable surface for contact with the body of the infant or adult, and helps absorb any fluid that issues outside the pad.

Figure 2:
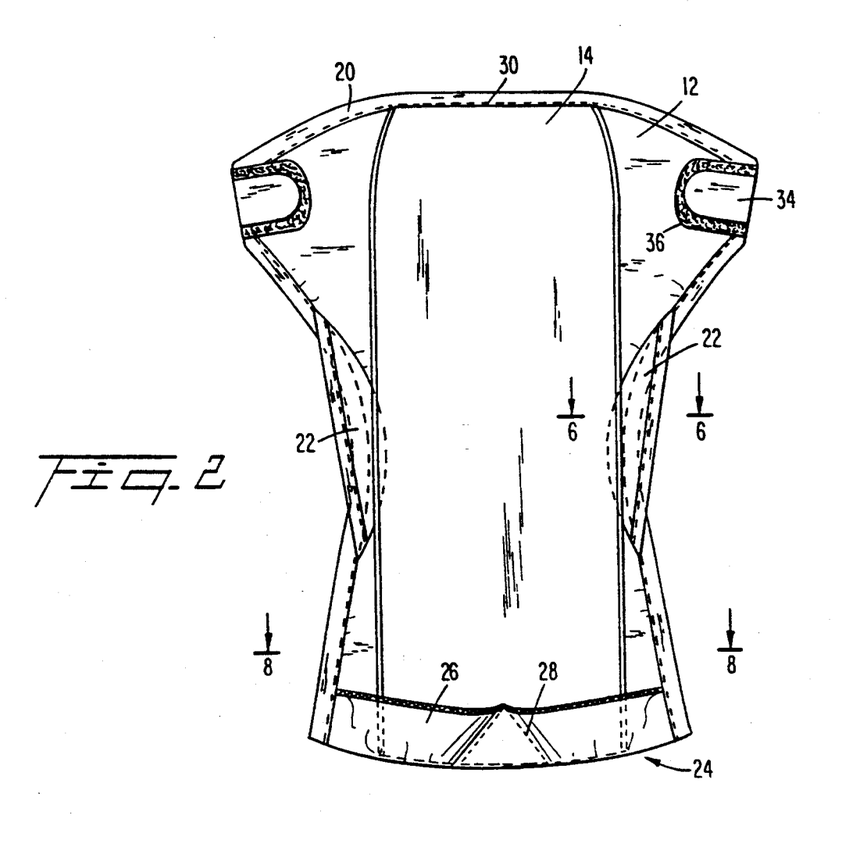
FIG. 2 is a view of the inner surface of the diaper, unfolded and with fastener tabs closed.

The diaper shell 12 initially is in the shape of an hourglass with its edge wrapped by the trim 20. This is shown in FIGS. 2 and 6, with a residual portion at each side of the shell forming web 22 that will define leg openings and rest against the thighs of the infant or adult when the diaper is worn.

One end of the shell at 24 is folded to the inner surface of the diaper to create a pocket 26 receiving one end of the pad 14. This end of the pad 14 is retained to the pocket 26 by stitching 28, which preferably is in the form of a V-shaped run of stitching shown in FIGS. 2 and 8. The other end of the pad 14 is retained to the diaper shell by transverse stitching 30 at the folded trim 20. As the diaper pad 14 is retained to the shell 12 only at the ends of the pad, the remainder of the pad "floats" on the inner surface of the shell as shown in FIG. 7. This enables the pad 14 to be retained with the shell so that the two will not separate during washing, but avoids the necessity to penetrate the waterproof shell with additional stitching. The pad 14, floating on the interior surface of the diaper shell 12, dries more quickly after washing because both the upper and lower surfaces of the pad are exposed to air.

The pocket 26, positioned on the frontal portion of the shell 12, is stitched to the shell only at its sides. This enables the pocket to catch fluid spreading from the stomach, and prevents wetting of surrounding bedding and of the wearer's garment. Fluid is further retained in the pocket by the trim 20 wrapped along the edge of the fold. The V-shaped stitching 28 at the central portion of the pocket 26 directs fluid laterally from the stomach of the infant or adult, to the sides of the diaper to further limit spreading of fluid over the stomach.

Figure 3:
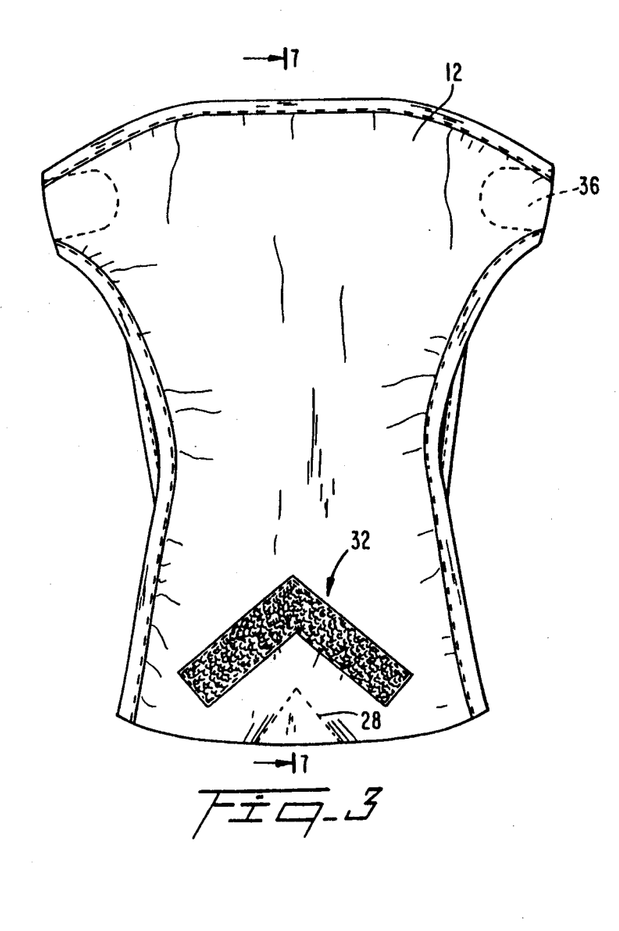
FIG. 3 is a view of the outer surface of the diaper, unfolded to show the V-shaped fastener region.
Figure 4:
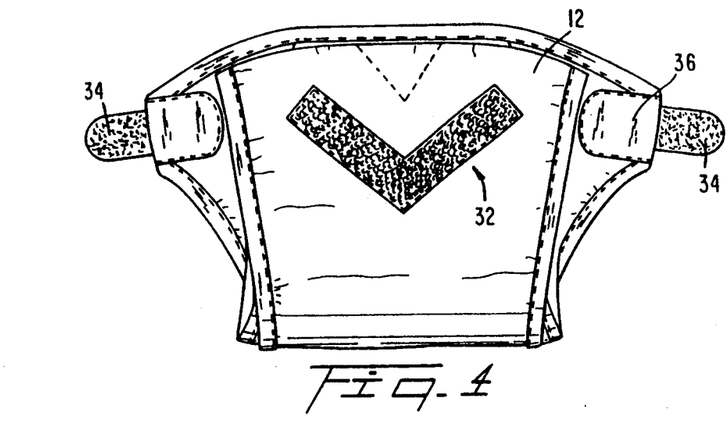
FIG. 4 is a view of an upper portion of the diaper, with fastener tabs open and in position to be coupled to the V-shaped fastener region.

Referring to FIG. 3, at the front of the diaper shell 12 is a region of strips 32 carrying filamentary fastener material, preferably loop, arranged in the form of a "V". The orientation of the "V" near one end of the diaper shell 12 corresponds to the orientation of the V-shaped stitching 28 that retains the pad 14 in pocket 26 inside the diaper. An example of strips 32 is Velcro® type filamentary fastener material; preferably two strips are oriented at a right angle to each other as shown. At the opposite end of the diaper, a pair of filamentary fastener tabs 34 (see FIG. 4) extends from truncated corners of the shell. The tabs 34 carry filamentary fastener material, preferably hook, and are adapted to wrap to the front of the diaper and to be coupled to fastener region 32 when the diaper is worn, as shown in FIG. 5. The diaper can be "sized" to the infant or adult by positioning the tabs 34 at the proper places on the fastener region 32.

Adjacent each tab 34, and stitched to the inner surface of shell 12, is a cover strip 36 formed of filamentary fastener material, preferably loop, adapted to receive and couple to tab 34 during washing. The tab 34 is manually folded into the position shown in FIG. 2, in contact with cover strip 36 to prevent filamentary hook material of the tab from accumulating lint during washing. As the base of the tab 34 is formed preferably of nylon or an equivalent material, the tab will tend to retain its fold as a result of continuing exposure to heat during several washings. Over time, the tabs 34 will tend to self-close to the cover strips 36 to eliminate the requirement of manual folding.

Cover strip 36 is slightly larger in surface area than fastener tab 34, as shown in FIG. 2. This provides two important functions. First, the cover strip 36 is large enough to ensure that all the filamentary hook material on tab 34 is covered when the tab is in a closed position for washing, shown in FIG. 2, even if the tab is slightly misaligned on the cover. Second, the larger surface area 36 enables the cover and tab to be assembled to the diaper shell 12 in a single stitching operation; this shall now be described with reference to FIGS. 9A-E.

Figure 9A:
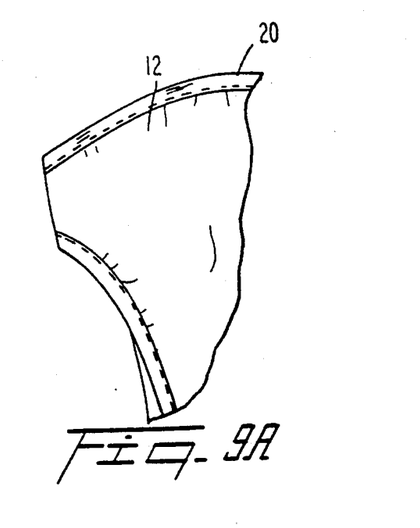
FIG. 9A shows a first step of manufacturing a portion of the diaper in accordance with the principles of the invention.
Figure 9B:
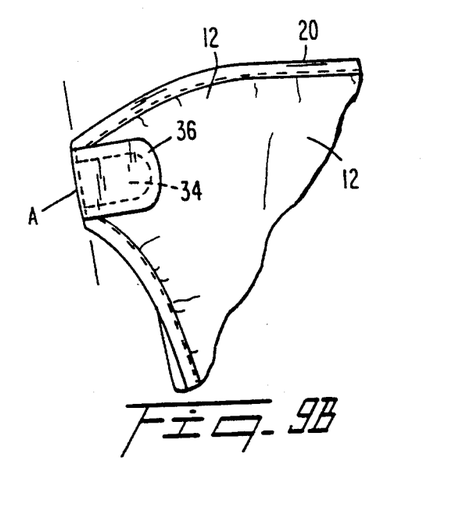
FIG. 9B shows a second step of manufacturing a portion of the diaper in accordance with the principles of the invention.
Figure 9C:
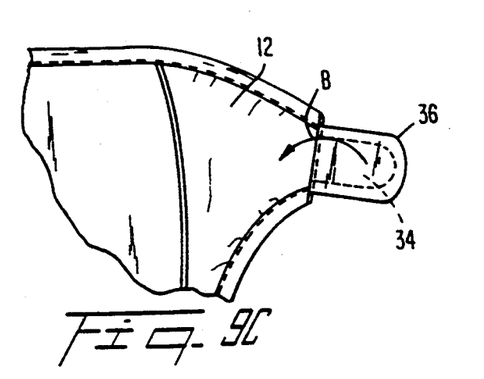
FIG. 9C shows a third step of manufacturing a portion of the diaper in accordance with the principles of the invention.
Figure 9D:
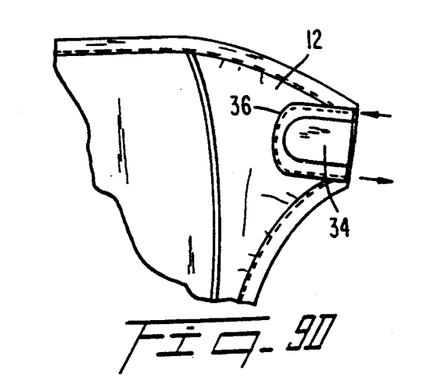
FIG. 9D shows a fourth step of manufacturing a portion of the diaper in accordance with the principles of the invention.
Figure 9E:
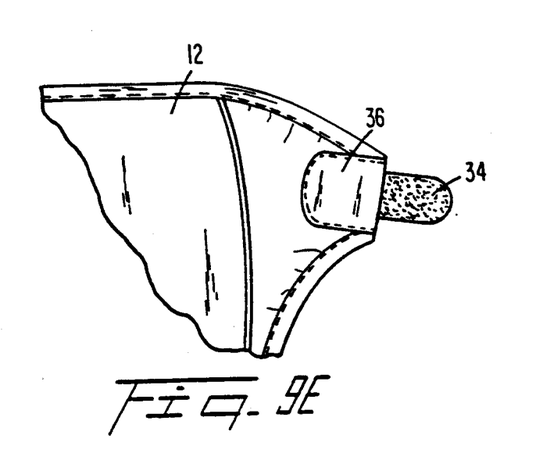
FIG. 9E shows a fifth step of manufacturing a portion of the diaper in accordance with the principles of the invention.

As a first step, shown in FIG. 9A, the diaper shell 12 already assembled of layers 16, 18 and trim 20 is oriented with its outer surface exposed and with the raw edge of the truncated corner positioned as shown. Next, in FIG. 9B a tab 34, die-cut to have a rounded edge, is positioned beneath a cover strip 36 on the outer surface of the diaper, with edges aligned with the edge of the shell. The shell and cover in this position are facing one another, temporarily coupled together by hook and loop filamentary materials. The inner edge of the tab-cover assembly is stitched to the shell along line A and the assembly is turned to the interior surface of the shell, with the corner of the diaper shell having the stitch forming a "hinge", as shown in FIGS. 9C and 9D. In FIG. 9D, the cover strip is positioned on the interior surface of the diaper shell, and the fastener tab 34 is coupled on top. The stitch made in FIG. 9B is now continued along the periphery of only the cover strip 36 as shown in FIG. 9D; this is possible since the cover strip is slightly larger than the tab. The tab 34 may now be opened to the position shown in FIG. 9E.

Attachment of the tab 34 and cover strip 36 to the diaper shell in the manner shown in FIGS. 9A-9D produces a sealed corner, with no raw edges of the tab, cover or diaper shell exposed. As the tab 34 and cover 36 are sewn to the corner of the diaper shell using a single, continuous stitching operation during construction, the cost of producing the diaper is minimized.

Figure 1:
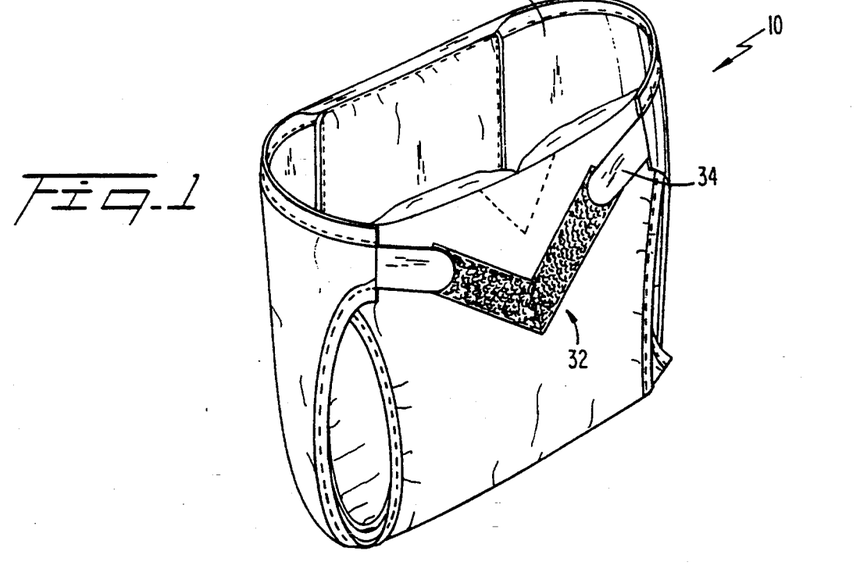
FIG. 1 is a perspective view of one embodiment of a reusable diaper produced in accordance with the principles of the invention and folded into position to be worn.
Figure 10:
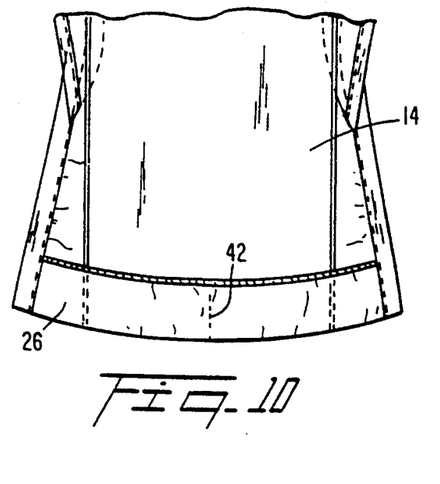
FIG. 10 is a view of the exterior surface of a portion of the diaper constructed in accordance With a second embodiment of the invention.
Figure 10A:
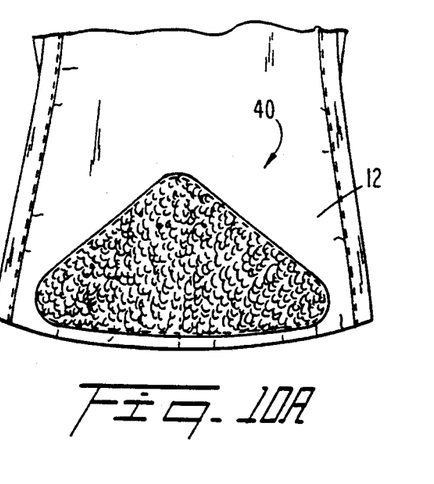
FIG. 10A is a view of the exterior surface of a portion of the diaper constructed in accordance with a second embodiment of the invention.

FIGS. 10 and 10A show another embodiment of the invention wherein filamentary fastener region 40, corresponding to region 32 in FIG. 1, has a triangular configuration. Filamentary region 40, formed of loop-type filamentary material, preferably is die-cut and stitched to the exterior surface of the frontal portion of the diaper shell 12. The construction of shell 12, with waterproof and cloth layers, in this embodiment and the embodiments that follow, is the same as in FIGS. 1–9. The corners of the triangular region 40 optionally are rounded. The triangular configuration is advantageous over the V-configuration of region 32 in FIG. 1 because the fastener tabs 34 can be coupled to a wider range of positions in the region 40. The diaper accordingly can be adjusted more comfortably to the wearer and applied more quickly.

One end of absorbent pad 14 is retained to diaper shell 12, within pocket 26, by a single line of stitching 42. This is in contrast with the V-shaped run of stitching 28 of FIG. 2 which in that embodiment is configured for consistency with the V-shaped filamentary fastener region 32 on the frontal portion of the diaper. The single line of stitching 42 is sufficient to securely retain the pad 14 to diaper shell 12. The opposite end of the pad 14 is stitched to a folded trim at the edge of shell 12 as provided in FIG. 2.

Figures 11, 11A:
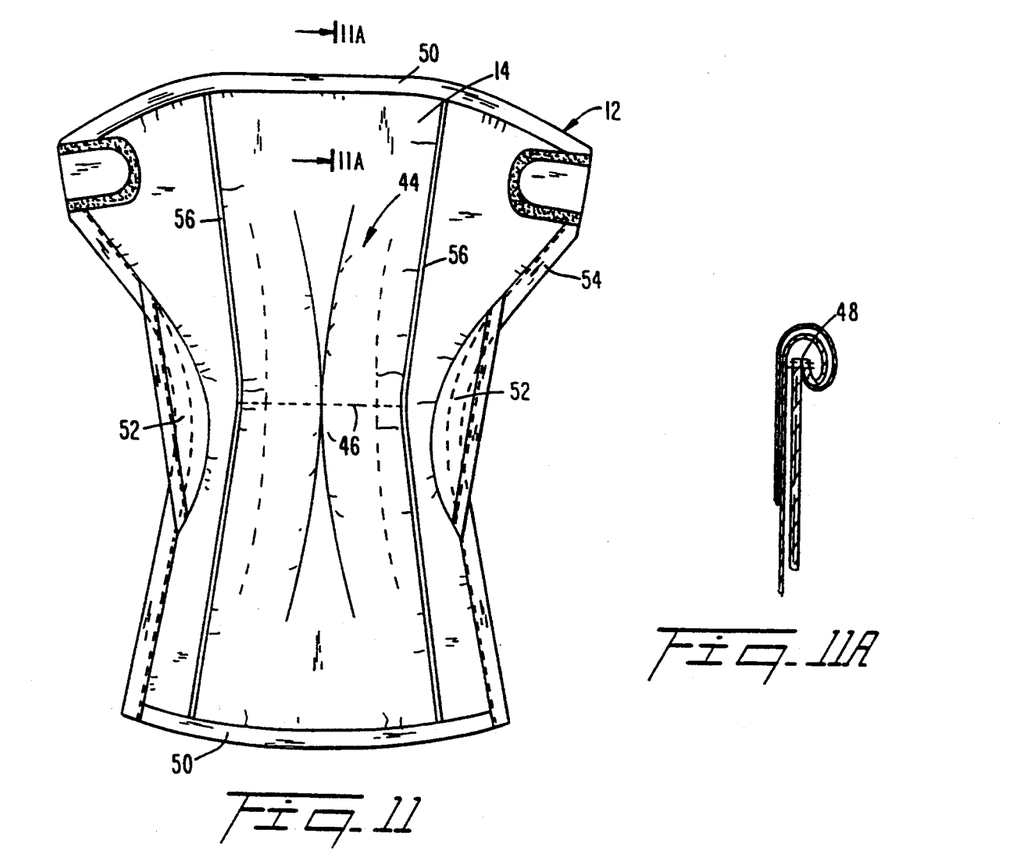
FIG. 11 is a view of the interior surface of a diaper having a tucked absorbent pad and waterproof side gussets in accordance with a third embodiment of the invention.
FIG. 11A is a cross-sectional view of the diaper taken along the line 11A—11A in FIG. 11.

In another embodiment, shown in FIGS. 11 and 11A, the pad 14, retained only at its upper and lower ends to the diaper shell 12, "floats" on the interior surface of the shell in the same manner as the embodiment of FIGS. 1–9. Advantageously, the central portion of the pad 14 is "tucked" at 44 by transverse stitching 46. This tuck 44, forming a central region of enhanced thickness of the pad, cups the groin and substantially improves fluid encasement.

The length of the pad 14 in the embodiment of FIG. 11 and 11A is slightly less than that of diaper shell 12. The upper and lower ends of shell 12 initially are placed in a reverse or "inside-out" orientation, with "wrong sides" stitched together. Then, the shell and pad are inverted so that the pad falls on the interior surface of the shell, as shown in FIG. 11A with the "right sides" of the pad and shell facing the wearer. The raw edges of the shell and pad accordingly become encased by the shell, sealed from view.

An advantage of the construction shown in FIGS. 11, 11A, is that the ends of the absorbent pad 14 are displaced from the ends of the diaper shell 12. The ends of the shell 12 form fluid flow barriers, restraining flow of fluid to the body of the wearer, shown as 50 in FIG. 11. The effect is enhanced by the thickened central region of the pad created by the tuck 44 which draws fluid inward from the sides of the pad.

The tuck 44 bows the sides of the pad 14 inward to establish an hour-glass form. Waterproof gussets 52, similar to gussets 22 shown in FIG. 2, cup the groin and comfortably enclose the thighs of the wearer. Raw edges of the shell and pad are encased by trim 54, 56.

Figure 12:
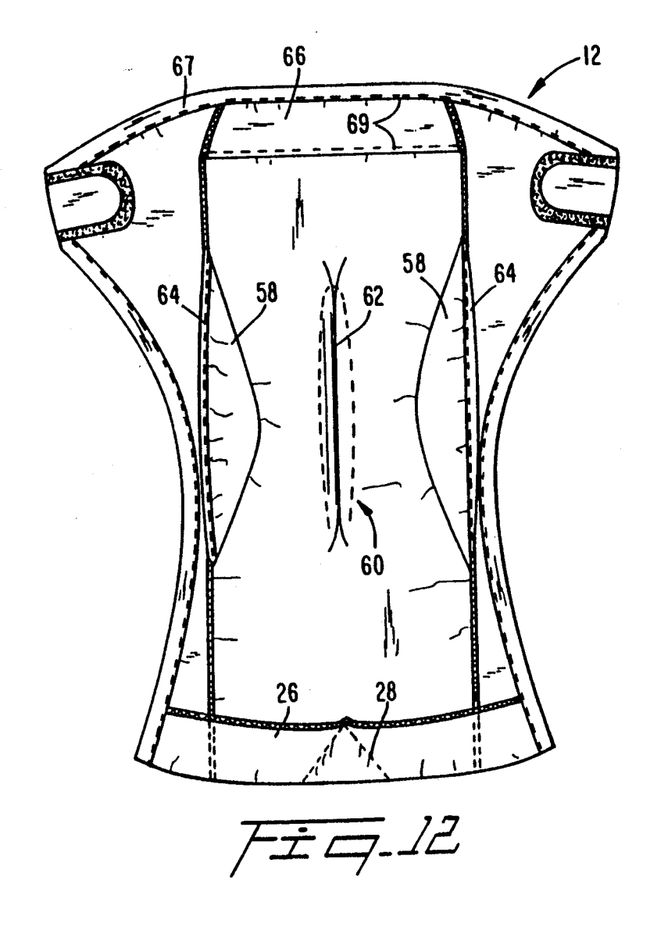
FIG. 12 is a view of the interior surface of a diaper having a construction to enhance fluid encasement in accordance with a fourth embodiment of the invention.

In another embodiment of FIG. 12, waterproof gussets 58 are stitched to the sides of pad 14, conforming to the hour glass shape created by tuck 60. The tuck 60 is formed in pad 14 by longitudinal stitching 62, facing the shell, although transverse stitching could be employed.

One end of pad 14 is retained to diaper shell 12, within pocket 26, by stitching 28. The opposite end of the pad is attached to the shell 12 through a length of waterproof material 66. The waterproof material 66, which may be formed of the same material as shell 12, establishes a fluid isolation barrier, or "bumper," to prevent body fluids from leaking to the back of the wearer through folded trim 67. Attachment of the bumper 66 to shell 12 and pad 14, beneath trim 67, is by stitching 69 which tends to enhance the fluid isolation effect.

The combined length of the pad 14 and bumper 62 is slightly less than the length of shell 12 beneath them. Hence, the shell will tend to "bow" along its length around the pad and bumper cupping the groin. Bowing is enhanced by trim 64, encasing the edges of gussets 58, and made of an elastic material. Fluid is encouraged to flow to and become absorbed in the central portion of the pad 14 by combined effect of bowing of the diaper, the gussets 58 and the tuck 62.

Figure 13:
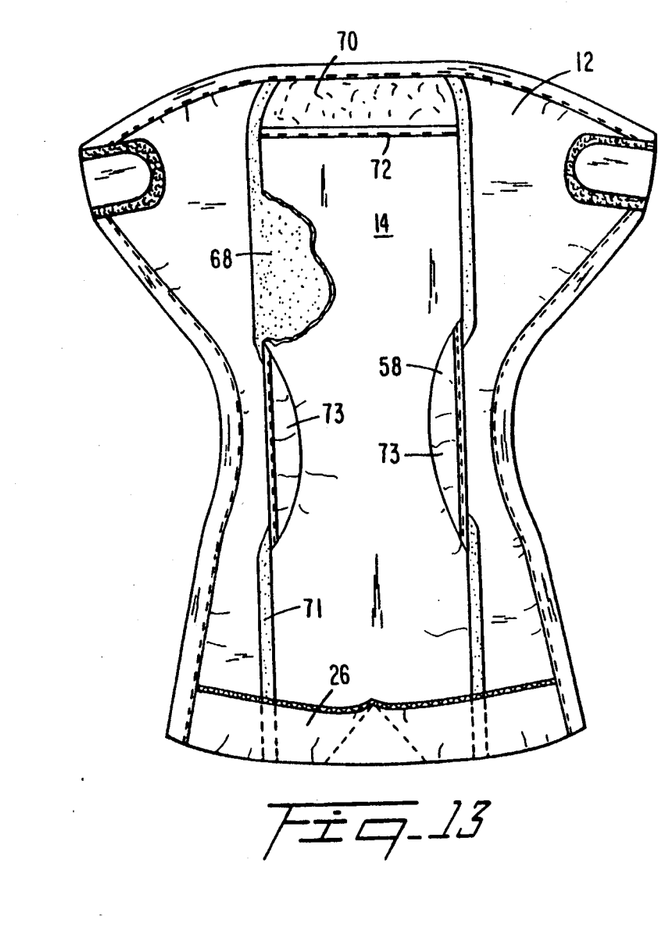
FIG. 13 is a view of the interior surface of a diaper having a waterproof "sling" underlying the fluid absorbent pad in accordance with a fifth embodiment.

In another embodiment of FIG. 13, the absorbent pad 14 is mounted on a "sling" 68, formed of waterproof material and attached, only at its upper and lower ends, to the diaper shell 12. The width of sling 68 is slightly greater than the width of pad 14, enabling the sides of the sling to be rolled inward and stitched to the pad at 71. Regions 71 form fluid barriers on the sides of the pad, preventing moisture from migrating laterally from pad 14 to the shell 12. Waterproof gussets 73, which further entrap fluid and establish a "containment pocket," are formed on the sides of pad 14 at regions 71. The seams between the pad 14 and shell are formed with the pad and shell initially in an inverted orientation with or without gussets 73, like that described for FIGS. 11, 11A, to encase the raw edges. In addition, the length of the waterproof sling 68 is greater than that of the pad 14. Whereas the pad 14 and waterproof sling 68 are sewn to the lower end of shell 12, beneath pocket 26, the upper end of the sling extends beyond the end of the pad to form bumper 70. Bumper 70 corresponds in function to bumper 66 in FIG. 12.

The upper end of pad 14 is stitched to the sling 68 at stitch line 72. The length of the sling 68 is slightly greater than that of shell 12 so that the shell will tend to become slightly bowed along its length to cup the groin of the wearer.

Figure 14:
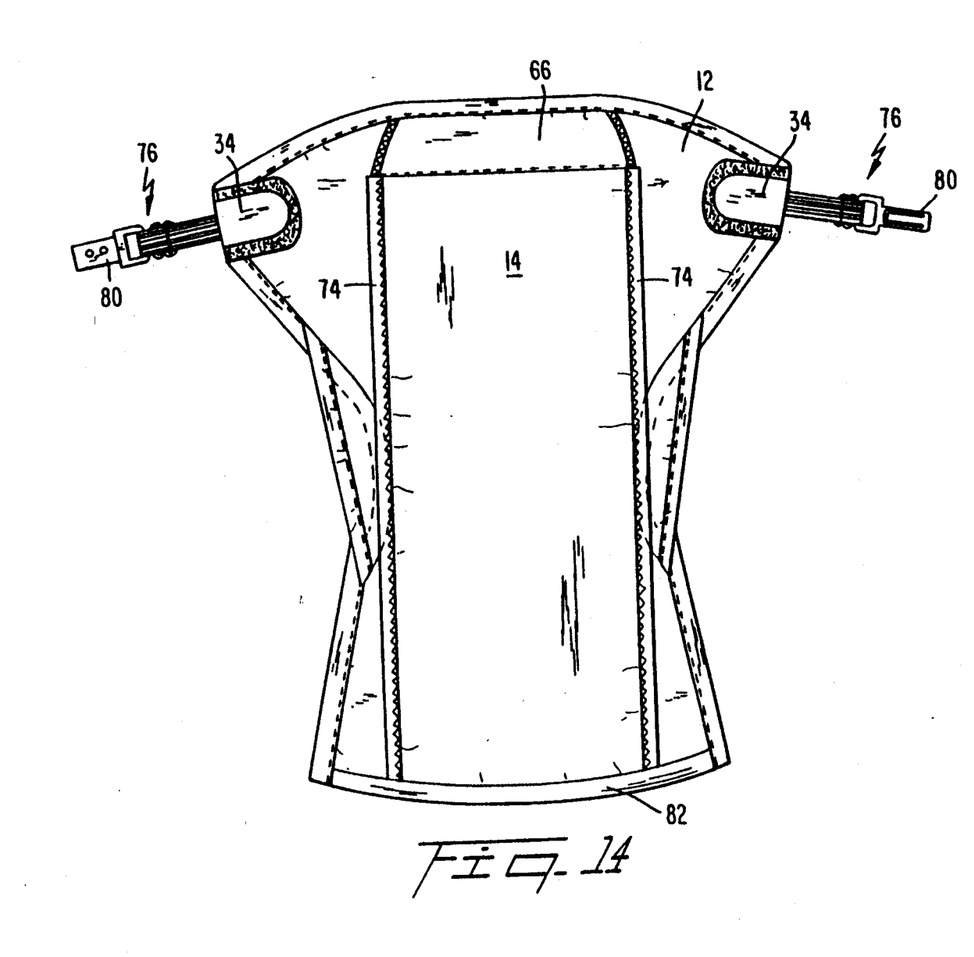
FIG. 14 is a first view of a sixth embodiment of the invention including an additional belt and fastener assembly as a safety feature to retain the diaper to an infant or adult.

FIG. 14 shows another embodiment wherein absorbent pad 14 is isolated from the frontal portion of diaper shell 12 by a waterproof bumper 66 stitched to the pad. The sides of the pad 14 are encased by an elastic scrim 74 that fits tight to the groin of the wearer, cupping the groin and encasing fluid within the pad.

The length of pad 14 is less that the length of diaper shell 12, to enable the lower end of the shell to be rolled inward, as shown at region 82, and stitched to the pad. Stitching is carried out in the manner shown in FIG. 11A to maintain the raw edges of the shell and pad encased by waterproof material. The region 82 of the diaper shell, together with bumper 66, form a waterproof barrier between the pad and shell at the frontal and rear portions of the diaper.

An important feature of the embodiment of FIG. 14 is in a belt and fastener assembly 76, supplementing fastener tabs 34 to retain the diaper to the body of an infant or adult. As shown in FIG. 14B, at each side of diaper shell 12 the assembly 76 comprises an elastic strap 78 having one end stitched to tab 34 or to the shell 12 and terminating at a fastener 80. The fastener 80 may be of any kind suitable to releasably couple the two straps 78, 78 to each other. In the embodiment of FIG. 14, the fastener 80 is a common plastic latch type fastener, shown coupled in FIG. 14A.

Figure 14A:
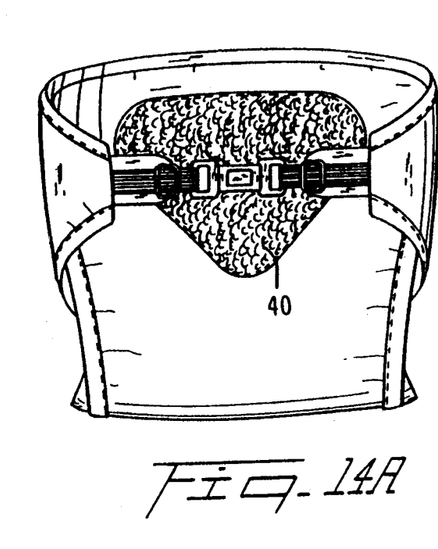
Figure 14B:
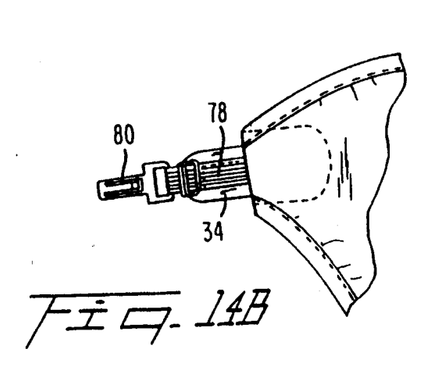

Referring to FIG. 14A in more detail, filamentary fastener region 40, on the frontal portion of the diaper shell 12, has a triangular shape, similar to the embodiment of FIG. 10. The diaper is fitted to the infant or adult by locating fastener tabs 34 on convenient portions of the region 40. The purpose of the strap and buckle assembly 76 is to retain the diaper to a toddler capable of removing the diaper at the fastener tabs 34, and possibly pulling the diaper over his head. This must be avoided particularly since the pad 14 may be laden with fluid, encased by waterproof bumper 66 and portion 82 of the diaper shell.

Figure 15:
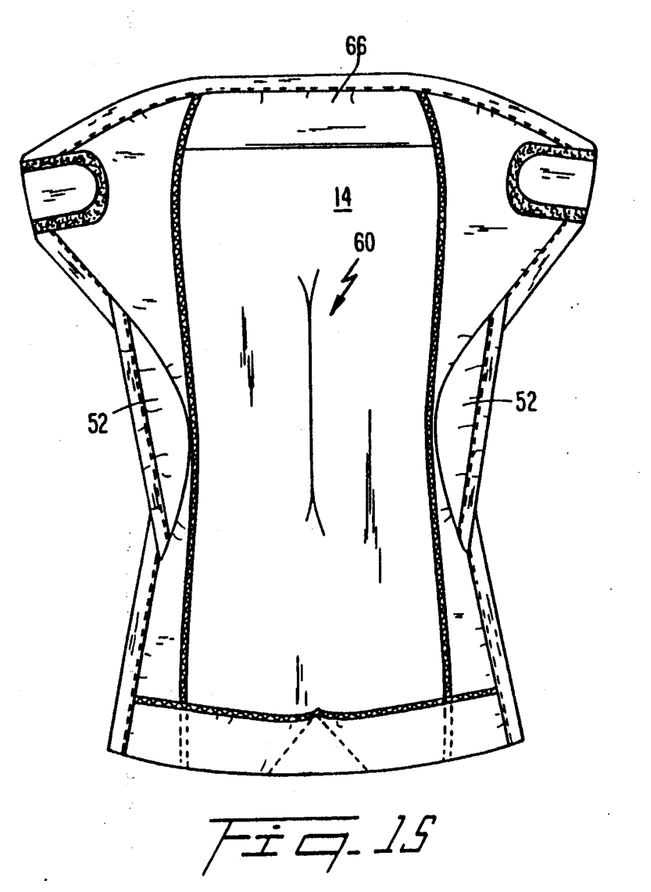
FIG. 15 is a view of a seventh embodiment of the invention including a fluid isolating "bumper" coupling the upper end of the fluid absorbent pad to the diaper shell.

In another embodiment of FIG. 15, the central region of fluid absorbent pad 14 is thickened by a tuck 60, formed by longitudinal stitching along the interior surface of the pad, in the same manner as in FIG. 12. The tuck 60 imparts a slight hourglass shape to the pad 14, conforming to gussets 52 that are formed in opposite sides of the shell. The gussets 52 are formed in shell 12 in a manner similar to that shown in FIG. 11. The upper end of pad 14 is isolated from the shell 12 by waterproof bumper 66, constructed in the manner shown in FIG. 12.

Figure 16:
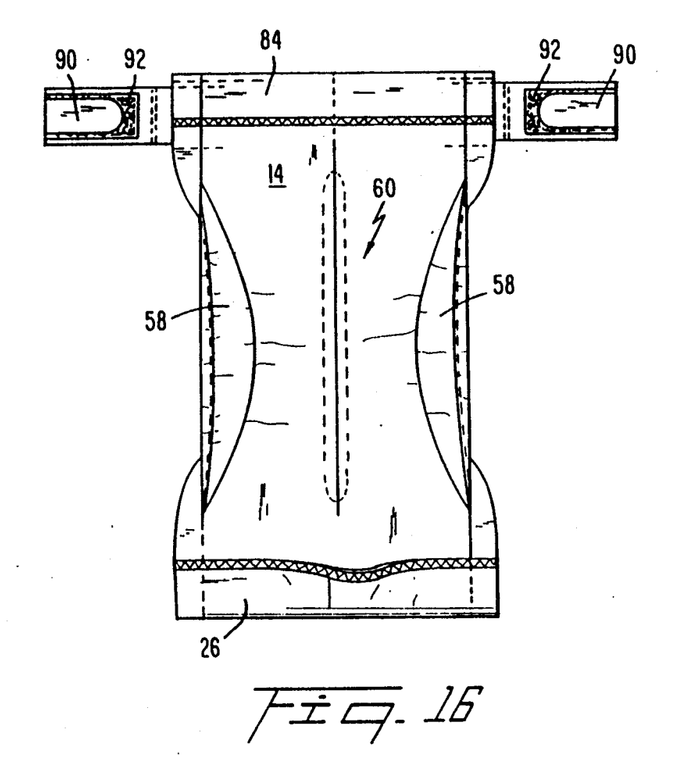
FIG. 16 is a view of the exterior surface of a diaper having an adjustable length belt in accordance with an eighth embodiment of the invention.

An additional embodiment of FIG. 16 is characterized by tuck 60 within pad 14 and waterproof side gussets 58, and the pocket 26 encasing the lower end of the pad similar to the embodiment of FIG. 12. The upper end of the absorbent pad 14 is encased by shell 12 which is turned inward and stitched to form region 84.

Figure 16A:
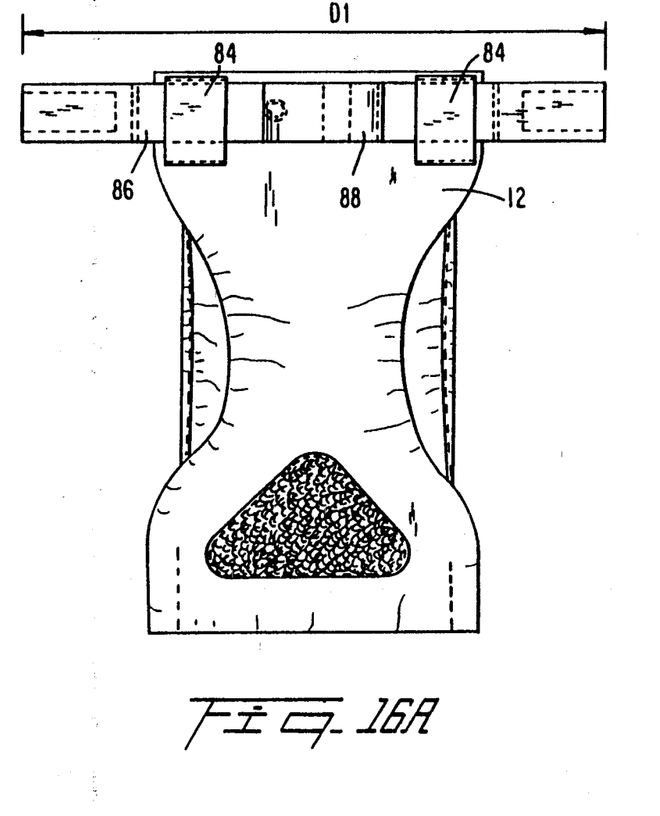
FIG. 16A is a view of the exterior surface of a diaper having an adjustable belt in accordance with the eighth embodiment of the invention
Figure 16B:
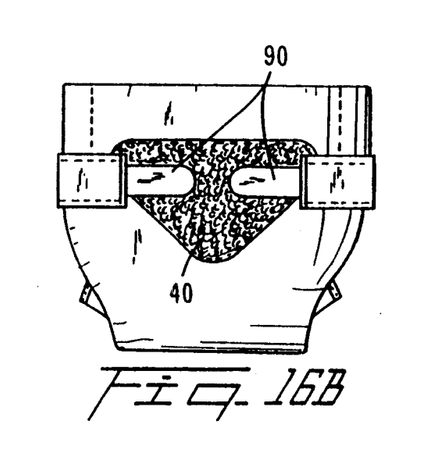
FIG. 16B shows a first view of belt is operated to adjust the size of the diaper.
Figure 16C:
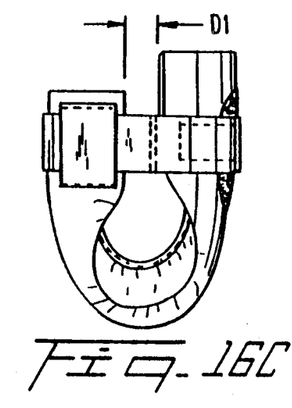
FIG. 16C shows a second view of how the belt is operated to adjust the size of the diaper.

Attached to the outer surface of the diaper shell 12 is a pair of loops 84 for retaining a belt 86. The belt 86 is formed of a length of continuous material secured to the shell at stitch line 88, as shown in FIG. 16A. At the ends of the belt 86 is a pair of fastener tabs 90 adapted to couple to filamentary fastener region 40 on the frontal portion of the exterior surface of the diaper shell 12. The region 40 preferably is formed with loop type filamentary material adapted to couple to hook type filamentary material on the tabs 90. Also on belt 86, adjacent tabs 90, are filamentary cover strips 92 shown in FIG. 16. The tabs 90 are stitched to the outer ends of the belt 84, facing inward as shown, to cause the tabs to self-close to cover strips 92 during washing in the manner described in my previous U.S. Pat. No. 4,537,591.

Figure 16D:
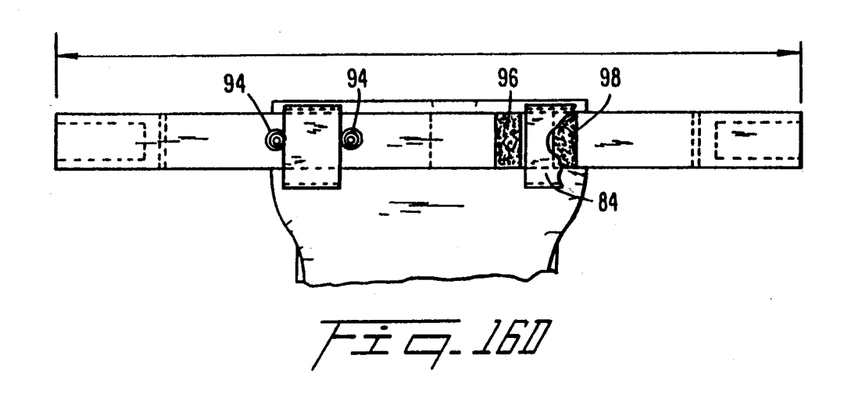
FIG. 16D shows a third view of how the belt is operated to adjust the size of the diaper.
Figure 16E:
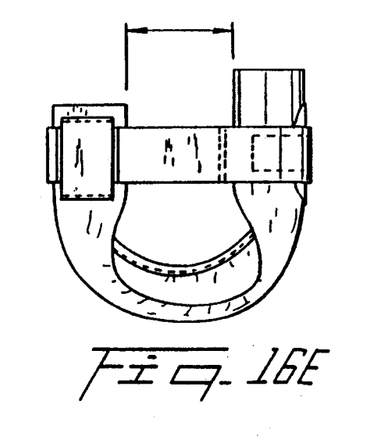
FIG. 16E shows a fourth view of how the belt is operated to adjust the size of the diaper.

In accordance with an important aspect of this embodiment, the length of belt 86 is adjustable using either one or both of the means shown in FIG. 16D. One means comprises a pair of snap fasteners 94 spaced along the axis of the belt. The second means comprises hook and loop filamentary fastener strips spaced along the belt. When the snaps 94 and strips 96, 98 both are coupled together, as shown in FIG. 16A, the length of the belt attains a value L1, so that the diaper attains a size D1, when worn, as shown in FIG. 6C. On the other hand, when the snaps 94 and strips 96, 98 both are decoupled from each other as shown in FIG. 16D, the length of the belt becomes enlarged to a value L2. This corresponds to an enlarged diaper size D2, as shown in FIG. 16E. An intermediate size can be attained by decoupling one or the other of the snaps and strips. Preferably, both adjustable means will be of the same type, snaps or straps. The size of the diaper accordingly can be adjusted, during growth of the infant or adult, by manipulating belt 84.

Advantageously, the strip of hook material 98 is positioned beneath loop 84 so that when the strips 96, 98 are decoupled from each other, the loop type filamentary material of strip 98 will be covered by the loop 84 and protected from accumulation of lint during washing.

Figure 17:
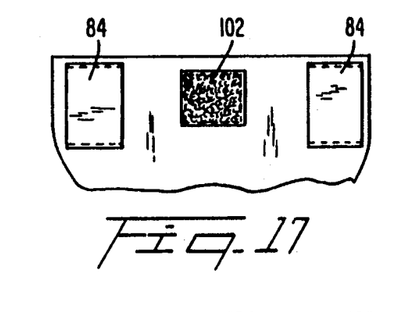
FIG. 17 is a view of a portion of a diaper having belt loops and a filamentary pad for retaining a belt to the diaper in accordance with a ninth embodiment of the invention.
Figure 17A:
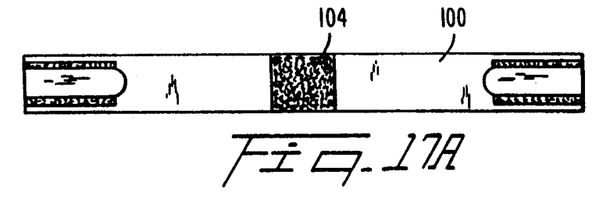
FIG. 17A is a view of a belt used in this embodiment.

In the embodiment of FIGS. 17, 17A, belt 100 may be separated from the diaper and replaced by a belt of a different size to fit the wearer. Belt 100 is adapted to fit to the waist of diaper shell 12, through loops 84. The belt 100 is retained in proper position to the shell by complementary filamentary strips 102 and 104.

Figure 18:
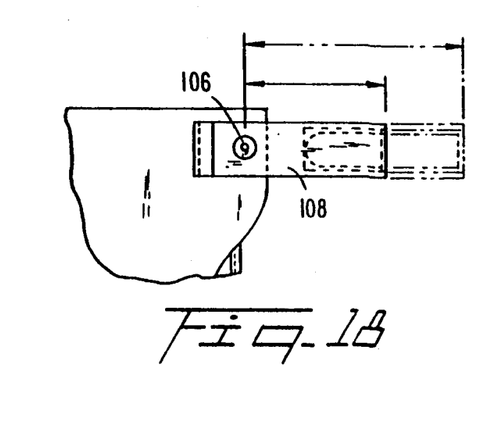
FIG. 18 is a view of a corner portion of a diaper having interchangeable size fastener tabs for variable sizing in accordance with a tenth embodiment of the invention.

In accordance with another embodiment, shown in FIG. 18, the belt may be formed of two straps, one on each side of shell 12, and coupled to the shell by a snap fastener 106 or the like. Depending on infant or adult size, a suitable pair of straps 108 can be selected from an inventory of straps, and snapped to the sides of the rear surface of the diaper.

In this disclosure, there is shown and described only the preferred embodiment of the invention, but, as aforementioned, it is to be understood that the invention is capable of use in various other combinations and environments and is capable of changes or modifications within the scope of the inventive concept as expressed herein.

What is claimed is:

1. A reusable diaper, comprising:
   a waterproof diaper shell; and
   a fluid absorbent pad retained only at upper and lower ends thereof to an inner surface of said diaper shell;
   an undersurface of said pad facing said shell being formed of a waterproof material;
   wherein at least one end of said fluid absorbent pad is attached to said diaper shell through a connecting piece of waterproof material and said pad waterproof undersurface is attached to said connecting piece, said waterproof connecting piece and undersurface together encasing and restricting fluid from leaving said pad and its undersurface.

2. The diaper of claim 1, wherein attachment of said connecting piece to at least one of said diaper shell and said pad is by stitching.

3. The diaper of claim 1, including gussets of waterproof material formed on the opposite sides of said pad, projecting upward from the surface of said pad to cup the groin area when worn.

4. A reusable diaper, comprising:
   a waterproof diaper shell;
   a fluid absorbent pad retained at an inner surface of said diaper shell, an undersurface of said pad forming a sling of waterproof material facing said waterproof diaper shell; and
   wherein the width of said sling is greater than the width of said pad, and opposite sides of said sling are free from and float upon the inner surface of said shell, and are turned inward and retain said pad to form fluid flow barriers at opposite sides of the pad.

5. The diaper of claim 4, including gussets of waterproof material formed on the opposite sides of said pad, projecting upward from the surface of said pad to cup the groin area when worn.

6. A reusable diaper, comprising:
   a waterproof diaper shell;
   a fluid absorbent pad retained at an inner surface of said diaper shell;
   only the upper and lower ends of said pad being connected to said diaper shell such that opposite sides of said pad remain free from and floating upon the inner surface of said shell; and
   waterproof gusset inserts having arcuate portions joined to the pad, projecting toward and cupping the groin of the wearer when worn.

7. The diaper of claim 6, including:

an elastic material attached to the opposite sides of said absorbent pad to conform the pad tight to the groin.

8. The diaper of claim 7, wherein each said gusset insert comprises a first arcuate side attached to said pad and an opposite side parallel to the corresponding side of said pad, said opposite side of said gusset having said elastic material.

9. The diaper of claim 6, wherein the surface of said pad facing said shell is waterproof.

* * * * *